United States Patent [19]

Wells, III et al.

[11] 4,110,298

[45] Aug. 29, 1978

[54] TRIOXANE PRODUCTION

[75] Inventors: William J. Wells, III, Houston; Adin Lee Stautzenberger, Corpus Christi, both of Tex.

[73] Assignee: Celanese Corporation, New York, N.Y.

[21] Appl. No.: 801,690

[22] Filed: May 31, 1977

Related U.S. Application Data

[63] Continuation-in-part of Ser. No. 718,638, Aug. 30, 1976, abandoned.

[51] Int. Cl.$^2$ ............................................. C07D 323/06
[52] U.S. Cl. ................................................... 260/340
[58] Field of Search ......................................... 260/340

[56] References Cited

U.S. PATENT DOCUMENTS 3,310,572  3/1967  Delle et al. ........................ 260/340
3,732,252  5/1973  Komazawa et al. ................. 260/340

FOREIGN PATENT DOCUMENTS 1,920,047  10/1970  Fed. Rep. of Germany ........... 260/340

OTHER PUBLICATIONS

Ullmann, Enzyklopadie der technischen Chemie, 3rd Ed., vol. 15, pp. 277-281, 301-303.

*Primary Examiner*—Norma S. Milestone
*Attorney, Agent, or Firm*—Stewart N. Rice; Ralph M. Pritchett

[57] ABSTRACT

In a process for the manufacture of trioxane by the distillation of aqueous formaldehyde solutions which are intimately mixed with an immiscible, non-volatile, oily liquid phase, the improvement comprising using a monoalkyl ether of a polyoxyalkylene glycol as the oily phase.

6 Claims, No Drawings

TRIOXANE PRODUCTION

This is a continuation-in-part of patent application Ser. No. 718,638, filed Aug. 30, 1976, now abandoned.

BACKGROUND OF THE INVENTION

The present invention relates to an improved process for the manufacture of 1,3,5-trioxane, also known as sym-trioxane, and which is referred to in the present specification and claims as "trioxane".

The manufacture of trioxane by distilling aqueous formaldehyde solutions in the presence of an acid catalyst is old and well known in the art. It is also known to accomplish the distillation of the aqueous formaldehyde solution while the latter is intimately mixed with an immiscible, non-volatile, oily liquid phase. For example the use of an oily phase consisting of a diester of o-phthalic acid is disclosed in U.S. Pat. No. 3,637,751 issued Jan. 25, 1972, to Fuchs, et al. U.S. Pat. No. 3,310,572 issued Mar. 21, 1967, to Delle, et al., discloses the use of liquid paraffin as well as synthetic lubricating oils, such as polypropylene glycols, as the oily phase. It is to such a type of process wherein the oily phase is substantially non-volatile and substantially inert under the conditions of the distillation that the present invention is directed.

Although various compounds have been disclosed in the literature as the oily phase in a process of the foregoing type, each has some disadvantages. Despite the drawbacks of some of the particular oily phases described in the prior art, many advantages are to be gained by their use, and thus the discovery of new and improved compounds for use as the oily phase is desired.

It is thus an object of the present invention to provide a new and useful process for the manufacture of trioxane. It is a particular object to provide an improvement in the processes as described above wherein trioxane is produced by distillation of an aqueous formaldehyde solution while it is intimately mixed with a non-volatile, immiscible, oil liquid phase. Additional objects will become apparent from the following description of the present invention.

SUMMARY

The present invention in one of its aspects as an improvement in a process for the manufacture of trioxane wherein the trioxane is produced by the distillation of an aqueous formaldehyde solution in the presence of an acid catalyst and while intimately mixed with an immiscible oily liquid phase, said oily liquid phase being inert and non-volatile under the conditions of said distillation, which improvement comprises utilizing a said oily liquid phase comprising a polymer which is a monoalkyl ether of a polyoxyalkylene glycol, said polymer being of the formula:

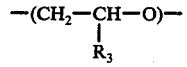

$$R_1 - O - (X) - R_2 \qquad I$$

wherein $R_1$ is hydrogen or an alkyl radical of from 1 to 20 carbon atoms and $R_2$ is hydrogen or an alkyl radical of from 1 to 20 carbon atoms, with one, but only one, of $R_1$ and $R_2$ being hydrogen, and wherein X is a divalent polyoxyalkylene radical containing repeating oxyalkylene units with from 50 to 100% of the repeating oxyalkylene units being of the formula:

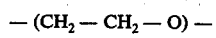

$$-(CH_2-CH-O)- \qquad II$$
$$\quad\quad\quad |$$
$$\quad\quad\quad R_3$$

wherein $R_3$ is a lower alkyl radical of from 1 to 6 carbon atoms with $R_3$ being alike or different on the several repeating units, and wherein the remaining 0 to 50% of the said repeating oxyalkylene units are oxyethylene units of the formula:

$$-(CH_2-CH_2-O)- \qquad III$$

said polymer being substantially water-insoluble and being liquid at atmospheric pressure at temperatures above about 80° C.

DETAILED DESCRIPTION OF THE INVENTION

From the foregoing summary it may be seen that the present invention resides in using an oily liquid phase which is a monoalkyl ether of a polyoxyalkylene glycol, said polymer being of Formula I set forth above. To be utilized in the present invention the make-up of the polymer must be such that it is substantially water-insoluble in order that it not dissolve to any appreciable extent in the aqueous formaldehyde solution, and that it be substantially nonvolatile and inert under the conditions of the distillation. By "inert" is meant that the polymer does not react to any substantial extent with itself or with the other reactants present during the distillation. It must also be a liquid under the conditions existing in the distillation vessel, it being preferred that the polymer be liquid at atmospheric pressure at temperatures above about 80° C. (it may also be liquid at temperatures below 80° C). The actual composition and molecular weight of the polymer can vary widely as long as the foregoing requirements of water-insolubility, nonvolatility, inertness, and liquidity be met. Some equilibrium interaction with the formaldehyde can be tolerated.

To be more specific, it is preferred that $R_1$ be hydrogen or an alkyl radical of from 1 to 20 carbon atoms, preferably 1 to 8 carbon atoms and that $R_2$ be hydrogen or an alkyl radical of 1 to 20 carbon atoms, preferably 1 to 8 carbon atoms. Either $R_1$ or $R_2$ must be hydrogen (most commonly $R_2$), but the remaining $R_2$ or $R_1$ must be an alkyl group to obtain optimum results.

At least 50% of the repeating oxyalkylene units in the polymer should be of Formula II above in order to assure that the polymer is water is insoluble. Oxyethylene units of Formula III can be present, but since these oxyethylene units contribute to water-solubility they must not be present to such an extent as to make the polymer water-soluble.

$R_3$ in Formula II above is a lower alkyl radical of from 1 to 6 carbon atoms. Preferably $R_3$ is a methyl radical or group such that the oxyalkylene radical is an oxypropylene radical. Other specific groups which $R_3$ may be include ethyl, n-butyl, iso-butyl, pentyl and hexyl. $R_3$ does not have to be the same on each repeating unit but can be different on the several units. For example on some of the units $R_3$ could be methyl, on some units ethyl, and the like. Where all of the $R_3$ radicals of the polymer are not the same, the oxyalkylene units containing the different $R_3$ radicals can be in block form or randomly mixed. This is true whether or not oxyethylene units are also present either in block form or randomly mixed. The molecular weight of the polymers utilized in the process of the present invention are generally on the order of about 250 to 5,000. Specific polyoxyalkylene glycols which may be utilized to form the ethers of Formula I above are polyoxypropylene glycol homopolymers, polyoxypropylene-polyoxyethylene glycol copolymers, polyoxypropylene-polyoxybutylene glycol copolymer, and the like. Most preferably the polymer is an ether of a polyoxypropylene glycol.

The ether, as explained above, should be a monoalkyl ether. The most preferred polymer for use in the present invention is a polymer which is a monobutyl ether of a polyoxypropylene glycol.

In conducting the distillation of the aqueous formaldehyde solution while mixed with the oily phase, sufficient stirring should be used to accomplish the intimate mixture of the two phases. Some references have stated that an emulsion results although whether or not a true emulsion results is not known. The two phases are however finely divided and mutually insoluble. The weight ratio of the oily liquid phase to the aqueous phase should in general be within the range of about 3:1 to 0.3:1, preferably about 0.5:1 to 1.5:1, more or less equal portions of each phase usually being utilized.

The distillation should be conducted at temperatures within the range of about 80° C. to 150° C., more preferably about 90° C. to 120° C., such temperature ranges being based on atmospheric pressure conditions. Of course if pressure other than atmospheric pressure is utilized, the boiling point will be affected. Pressures are conveniently atmospheric but subatmospheric or superatmospheric conditions may be utilized if desired. Conventional equipment may be utilized to accomplish the distillation of the aqueous formaldehyde solution, such as a distillation vessel or pot with a siphon reboiler. A siphon reboiler will promote mixing of the two phases and is therefore recommended.

The process may be conducted batchwise or continuously, although most industrial processes will be operated on a continuous basis with continuous removal of crude trioxane vaporized from the distillation vessel and fresh formaldehyde feed continuously passed to the vessel. In a continuous process there will also generally be recycled to the distillation vessel from the trioxame recovery system some aqueous formaldehyde as well as small amounts of trioxane. Even though the catalyst is not affected to any substantial extent by the distillation and does not volatilize under the conditions of the distillation, small amounts of catalyst will be lost by misting over, thus requiring addition of small amounts of make-up catalyst from time to time.

The acid catalysts that may be utilized to produce trioxane by the distillation of aqueous formaldehyde solutions are well known. Although acid ion exchange resins are known to be useful as catalysts, the acid catalyst generally utilized in the present process is one which is soluble in the aqueous formaldehyde solution. Particular catalysts which are suitable include acids such as sulfuric acid, phosphoric acid, methanesulfonic acid and p-toluenesulfonic acid. Other catalysts are also known and undoubtedly new catalysts will be discovered. The present invention does not, however, reside in discovery of any new catalysts and it is to be construed as covering all catalysts now known or hereafter discovered. The mineral acids are the preferred catalysts, with sulfuric acid being especially preferred. The amount of catalyst will vary according to the particular catalyst being utilized. When using sulfuric acid, the amount of catalyst should be such that the acid catalyst constitutes from about 2 to 10 weight percent, preferably 3 to 6 weight percent, of the aqueous formaldehyde phase of the reaction mixture. It is preferred that the catalyst be mixed with the aqueous formaldehyde solution prior to the mixing with the oil. If make-up catalyst is added directly to the distillation vessel, then it is preferred that the make-up catalyst be relatively dilute.

The aqueous formaldehyde solution passed to the distillation vessel should contain from about 30 to 90% by weight of formaldehyde, preferably from about 50 to 70% by weight of formaldehyde. For example in a typical process operated on a continuous basis, the fresh formaldehyde solution containing about 68% by weight of formaldehyde will be combined with a recycled stream containing about 55% by weight of formaldehyde to result in a feed containing about 58% by weight of formaldehyde.

In the reactor-distillation vessel formaldehyde will be converted to trioxane, and a crude tioxane will be removed as overhead vapors. In addition to trioxane, these overhead vapors will also contain amounts of formaldehyde and the like. Recovery of the trioxane can be accomplished by conventional physical methods such as rectification, crystallization, extraction, or combinations of these. If desired a distillation tower may be connected directly to the reactor-distillation vessel such that the overhead vapors of the distillation ascend directly into the distillation tower. The unreacted formaldehyde recovered from the recovery zone can be recycled to the distillation vessel.

When operating according to the present invention, improved results are obtained. One important benefit is a substantial increase in conversion of formaldehyde to trioxane per pass through the reactor-distillation vessel over that obtained in prior art processes, including those prior art processes utilizing an oily liquid phase. Another advantage of operating in accordance with the present invention is that the residence time of the aqueous formaldehyde solution in the distillation vessel is reduced by about 50% resulting in less byproduct formation, i.e., inefficiencies to formic acid, methanol and methyl formate. Also operation according to the present invention allows a more efficient and less energy intensive recovery system than could be utilized in the traditional formaldehyde distillation process wherein no oil is present.

In particular, when rectification of the crude trioxane vapors is accomplished as a part of the recovery process, the higher ratios of trioxane to formaldehyde which accompany the present invention allow correspondingly small reflux ratios to be applied to the distillation tower, which results in energy savings. Total formaldehyde concentration in the feed to the reactor-distillation vessel, fresh plus recycle, may exceed 59% without fear of paraformaldehyde precipitation as happens in the case of no oil being present, the precipitation being avoided probably because of the higher conversions involved. These higher allowed formaldehyde concentrations lead to at least two additional advantages, namely: (1) higher conversions, because there is a formaldehyde-trioxane equilibrium involved which is shifted in the favor of more trioxane production as the concentration of formaldehyde is increased, and (2) more economical operation, because higher concentrations of formaldehyde mean lower concentrations of water entering the reaction-recovery system and thus less energy expended in moving water from place to place. Smaller recycle streams are also present in a continuous process operated in accordance with the present invention, such being advantageous because of the smaller equipment that may be utilized.

While the exact mechanism whereby the present invention results in the benefits given hereinabove is not precisely known, sufficient facts have been gathered by the inventors to allow a hypothesis. It will be seen that the comments apply generally to all oily components used as second phases, the differences in their respective performances being one of degree; that is, degree to which they successfully participate in the following operations. Trioxane is known to be present only in very small amounts in solution at equilibrium; e.g., 2–4% (by weight) trioxane in an aqueous solution at 100° C. of 5% $H_2SO_4$ and, originally, approximately 60% formaldehyde. Owing to a tendency to form a minimum boiling point azeotrope of the approximate composition 70% trioxane and 30% water at about 91.5° C., trioxane is removed from solution at a faster rate than formaldehyde, upsetting the solution equilibrium in favor of more trioxane production. The net observed result is about a 25% conversion of formaldehyde to trioxane per pass at a one hour residence time. With a finely divided, second liquid phase present in the reactor-distillation vessel, trioxane molecules also have the opportunity to leave and upset the equilibrium of the aqueous phase by migration into the second liquid phase. Further, trioxane may completely escape the vessel by vaporization from the non-aqueous as well as the aqueous phase. The degree to which these operations will contribute to a higher observed net conversion will depend on (1) the distribution primarily of trioxane and also that of formaldehyde, water and others between the two phases under reaction conditions; (2) the relative vaporization rates of the important components from the non-aqueous phase; (3) the ease and degree of breakdown of the non-aqueous phase into a finely divided state with high surface area resembling an emulsion; (4) the degree to which the second phase interacts with the aqueous environment, both chemically and physically (solubility in the aqueous phase); and (5) also the degree of vaporization of the non-aqueous phase.

From several viewpoints—energy of vaporization, contribution of vapor pressure to reactor product (which results in suppression of trioxane vaporization), and difficulty of separation and recycle—it is advantageous that the second phase have essentially no vapor pressure under reaction conditions, i.e., it should be an "oil". The aqueous phase should not dissolve, chemically destroy, or overreact with the oil, on either a long or short term basis, such that the benefit of having a second or distinct liquid phase is lost. These positive contributions tend to be offset by the fact that more or less half of the aqueous phase, wherein trioxane is believed to be produced, has been replaced by the oily component, and thus for a given production rate the aqueous phase residence time, upon which the conversion is directly dependent, has been halved. It is believed that the examples which follow will show that the oily components of the present invention, as exemplified by the preferred mono-butyl ethers of polyoxypropylene glycols, will overcome the residence time constraint and result in significantly superior conversions when compared to no-oil operation and even when compared to operation with other oils such as the physically similar polyoxypropylene glycols. These latter are diols, and it is surmised that this feature gives these oils added undesirable aqueous phase solubility both through increased attraction to water and a higher equilibrium hemi-formal concentration through reaction with formaldehyde.

The following examples are given to illustrate the present invention, but are not to be construed as limiting the scope thereof. In the examples all parts and percentages are by weight unless otherwise specified.

EXAMPLE 1

A continuous reactor-distillation vessel was prepared consisting of an electrically-heated, single-leg, glass, siphon reboiler of approximately one liter total capacity. The vessel was then charged with about 250 ml. of a 51.3% aqueous formaldehyde solution to which was then added sufficient sulfuric acid to cause the sulfuric acid concentration to be about 4%. There was then added to the vessel about 250 ml. of a monobutyl ether of a polyoxypropylene glycol of the formula:

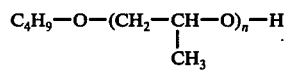

wherein "$n$" was such that the average molecular weight was about 2500. The vessel containing the two-phase mixture was then heated to boiling (109° C.) at atmospheric pressure, so as to vaporize the crude trioxane product. The siphon reboiler provided the necessary stirring for intimate mixing of the two phases.

The liquid level in the reactor-distillation vessel was maintained substantially constant by adding fresh aqueous formaldehyde feed at the same rate as crude trioxane vapors were removed. This rate was adjusted so that the residence time of the aqueous formaldehyde solution was about one-half hour based on the aqueous phase present, or about one hour based on the total volume of liquids in the vessel. The crude trioxane vapors were condensed to form a crude liquid product, which contained, by chemical analysis, about 32.1% formaldehyde and 19.0% trioxane, for a 30% conversion of formaldehyde to trioxane, defined as (% trioxane in product) 100 ÷ (% formaldehyde in the feed).

EXAMPLE 2

The procedure of Example 1 was repeated except that the oil utilized was a monobutyl ether of a polyoxypropylene glycol of average molecular weight about 2050, concentration of the aqueous formaldehyde was 59.9%, and the boiling temperature was 111° C. The crude liquid trioxane product contained about 35.0% formaldehyde and 24.1% trioxane for a 40.2% conversion as defined above.

EXAMPLE 3

The procedure of Example 1 was repeated except that the aqueous formaldehyde feed contained 72.1% formaldehyde and the boiling temperature was 109.2° C. The crude liquid trioxane product contained about 39.6% formaldehyde and 32.4% trioxane for a 44.9% conversion. Paraformaldehyde did not precipitate in the reaction medium even though the formaldehyde content in the feed was in excess of 70%.

Examples 1–3 show that conversion of formaldehyde to trioxane varies with formaldehyde concentration, increasing from about 30% to about 45% as formaldehyde feed concentration increased from about 51% to about 72%.

EXAMPLE 4

The procedure of Example 1 was repeated except that the oil utilized was a polyoxypropylene glycol with an average molecular weight of 2000, the concentration of the aqueous formaldehyde was 59.7%, and the boiling temperature was 102.2° C. The crude liquid trioxane product contained about 41.8% formaldehyde and about 17.7% trioxane for a 29.6% conversion of formaldehyde to trioxane. This is to be compared with 40.2% conversion obtained when using a monoetherified polyoxypropylene glycol in Example 2 under otherwise comparable conditions.

EXAMPLE 5

The procedure of Example 1 was repeated except that the oil utilized was a heavy paraffin oil, commonly called mineral oil, the concentration of the aqueous formaldehyde was 52.5%, and the boiling temperature was 90° C. The crude liquid trioxane product contained 40.6% formaldehyde and 11.9% trioxane for a 22.7% conversion of formaldehyde to trioxane.

EXAMPLE 6

The procedure of Example 1 was repeated except that no oil was added and the aqueous formaldehyde solution used as feed stock contained about 56.6% formaldehyde. Further, the volume of aqueous formaldehyde and sulfuric acid charged to the vessel was doubled because of the absence of the oil phase. The boiling temperature under these conditions was 100° C. The crude liquid trioxane product recovered from this run contained about 41.3% formaldehyde and 15.2% trioxane for a 26.8% conversion.

Examples 4, 5 and 6 are illustrative of the prior art. It may be seen that operation according to the present invention gives improved results over the prior art methods.

In Example 2 above, the oil phase employed was "UCON LB-1145", and in Examples 1 and 3 the oil phase was "UCON LB-1715". These are trade names of Union Carbide Corporation for polyoxypropylene glycol monobutyl ethers.

The following Examples 7 and 8 are given to illustrate that the improved results obtainable from use of the present monoalkyl ethers are not attained when one substitutes for them either a water-soluble polyalkylene glycol (Example 7) or a water-insoluble dietherified (s distinguished from monoetherified) polyalkylene glycol (Example 8). While it is not intended that the scope of the invention be restricted by this interpretation, it is believed that the unexpectedly improved results obtained with the present monoetherified polyalkylene glycols are related to their having in the molecule a hydrophilic and a hydrophobic end, while they are at the same time insoluble in the aqueous phase. This results in formation of small, thin-walled, spheroidal drops of the oily phase which resist coalescence and which provide, in their interiors, an environment which favors the trioxane-formation reaction.

EXAMPLE 7

The procedure of Example 1 was repeated except that the "oil" utilized was a water soluble polyoxyethylene glycol with an average molecular weight of 400, the concentration of the aqueous formaldehyde was 60.3%, and the boiling temperature was 107° C. The crude liquid trioxane product contained about 47.2% formaldehyde and 13.0% trioxane for a 21.6% conversion of formaldehyde of trioxane. The oil was completely soluble in the reaction mixture, and there was only one liquid phase apparent.

EXAMPLE 8

The procedure of Example 1 was repeated except the oil utilized was a dietherified polyoxypropylene glycol of the formula:

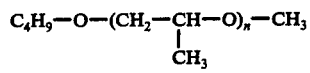

wherein "n" was such that the average molecular weight was about 2500, the concentration of the aqueous formaldehyde was 60.7% and the boiling temperature was 100.6° C. The crude liquid trioxane product contained about 44.2% formaldehyde and 16.4% trioxane for a 27.0% conversion of formaldehyde to trioxane.

The embodiments of the invention in which an exclusive privilege is claimed are defined as follows:

1. In a process for manufacturing trioxane which comprises distilling an aqueous formaldehyde solution intimately mixed with a substantially immiscible oily liquid phase in the presence of an acid catalyst, the improvement which comprises using as said oily liquid phase a monobutyl ether of polyoxypropylene glycol having an average molecular weight of from about 2050 to about 2500.

2. The improvement of claim 1 wherein said acid catalyst consists essentially of sulfuric acid.

3. The improvement of claim 1 wherein said distillation is conducted at temperatures within the range of about 90° C. to 120° C.

4. The improvement of claim 1 wherein the weight ratio of said oily liquid phase to said aquoues formaldehyde solution is within the range of about 0.3:1 to 3:1.

5. The improvement of claim 4 wherein the weight ratio of said oily liquid phase to said aqueous formaldehyde solution is within the range of about 0.5:1 to 1.5:1.

6. The improvement of claim 5 wherein the proportions of said oily liquid phase and said aqueous formaldehyde solution are approximately equal.

* * * * *